(12) United States Patent
Berger et al.

(10) Patent No.: US 7,818,318 B2
(45) Date of Patent: *Oct. 19, 2010

(54) METHOD AND SYSTEM FOR DATA CLASSIFICATION IN THE PRESENCE OF A TEMPORAL NON-STATIONARITY

(75) Inventors: Gideon Berger, New York, NY (US); Bhubaneswar Mishra, Great Neck, NY (US)

(73) Assignee: New York University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 12/352,444

(22) Filed: Jan. 12, 2009

(65) Prior Publication Data

US 2009/0182701 A1 Jul. 16, 2009

Related U.S. Application Data

(63) Continuation of application No. 10/276,429, filed as application No. PCT/US01/15140 on May 10, 2001, now Pat. No. 7,478,077.

(60) Provisional application No. 60/204,816, filed on May 17, 2000.

(51) Int. Cl.
G06F 7/00 (2006.01)
G06F 17/30 (2006.01)
(52) U.S. Cl. .................................. 707/725; 707/729
(58) Field of Classification Search ................ 707/725, 707/729
See application file for complete search history.

(56) References Cited

U.S. PATENT DOCUMENTS

| 6,138,117 | A | * | 10/2000 | Bayardo ............................. 1/1 |
| 6,208,720 | B1 | * | 3/2001 | Curtis et al. ........... 379/114.14 |
| 6,665,669 | B2 | * | 12/2003 | Han et al. ............................ 1/1 |
| 6,772,152 | B2 | * | 8/2004 | Wang et al. .................. 382/181 |
| 6,799,175 | B2 | * | 9/2004 | Aggarwal ............................ 1/1 |

OTHER PUBLICATIONS

Balaji Padmanabhan and Alexander Tuzhilin (2000), Small is Beautiful: Discovering the Minimal Set of Unexpected Patterns, pp. 54-63.*

* cited by examiner

*Primary Examiner*—Don Wong
*Assistant Examiner*—Merilyn P Nguyen
(74) *Attorney, Agent, or Firm*—Dorsey & Whitney LLP

(57) ABSTRACT

A method and system for determining a feature of a particular pattern are provided. In particular, data records are received, and predetermined patterns that are associated with at least some of the data records are obtained. Using the system and method, particular information is extracted from at least a subset of the received data records, the particular information being indicative of the particular pattern in at least some of the data records. Then, it is determined whether the particular pattern is an unexpected pattern based on the obtained predetermined patterns. In addition, it is possible to classify and reduce data and/or parameters provided in the data records. First, the data records are received. Then, the data records which have at least one particular pattern are classified using a Multivariate Adaptive Regression Splines technique. Thereafter, the data and/or parameters of the classified data records are shrunk using a Stein's Estimator Rule technique.

13 Claims, 10 Drawing Sheets

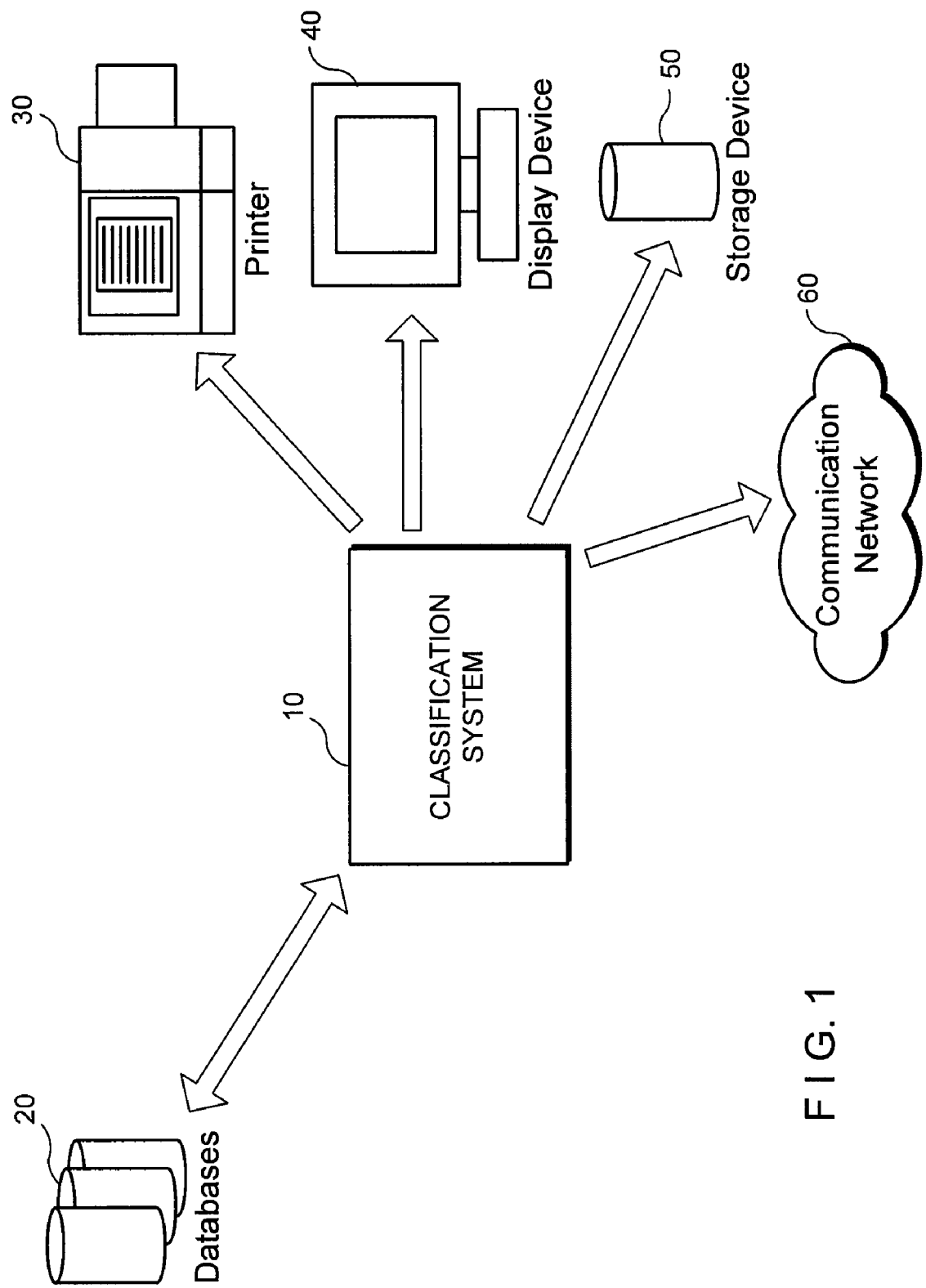
F I G. 1

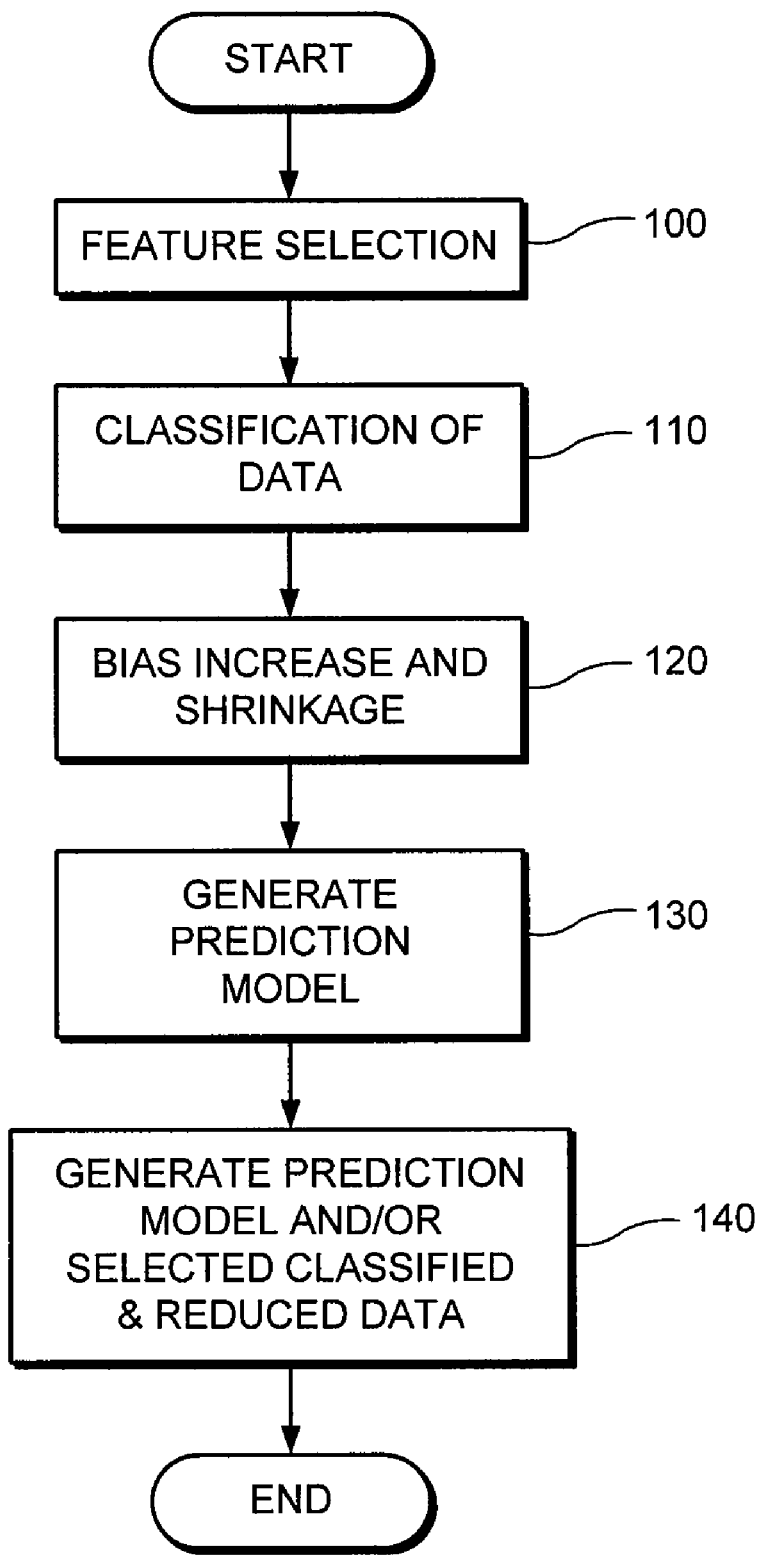
F I G. 2

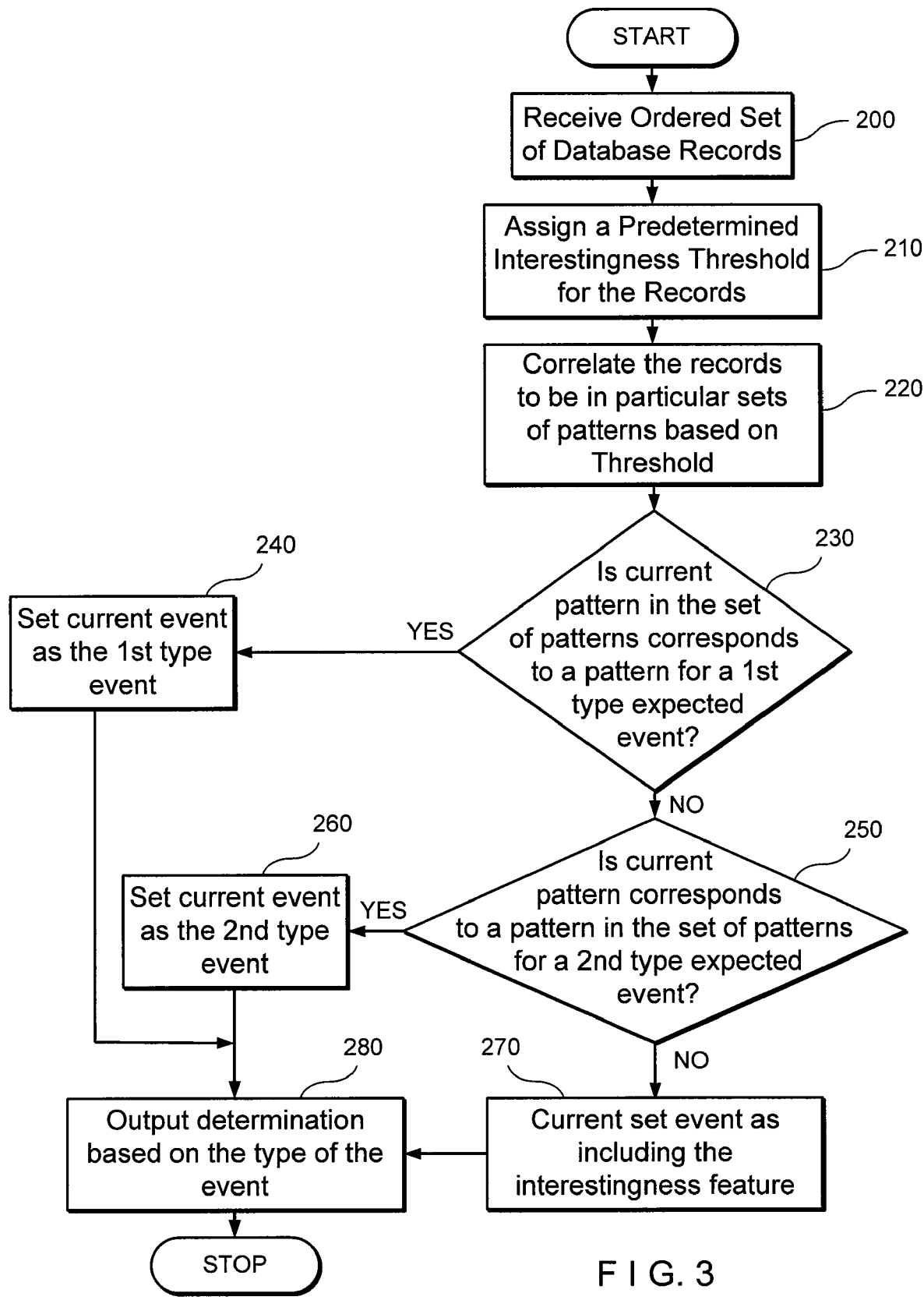
F I G. 3

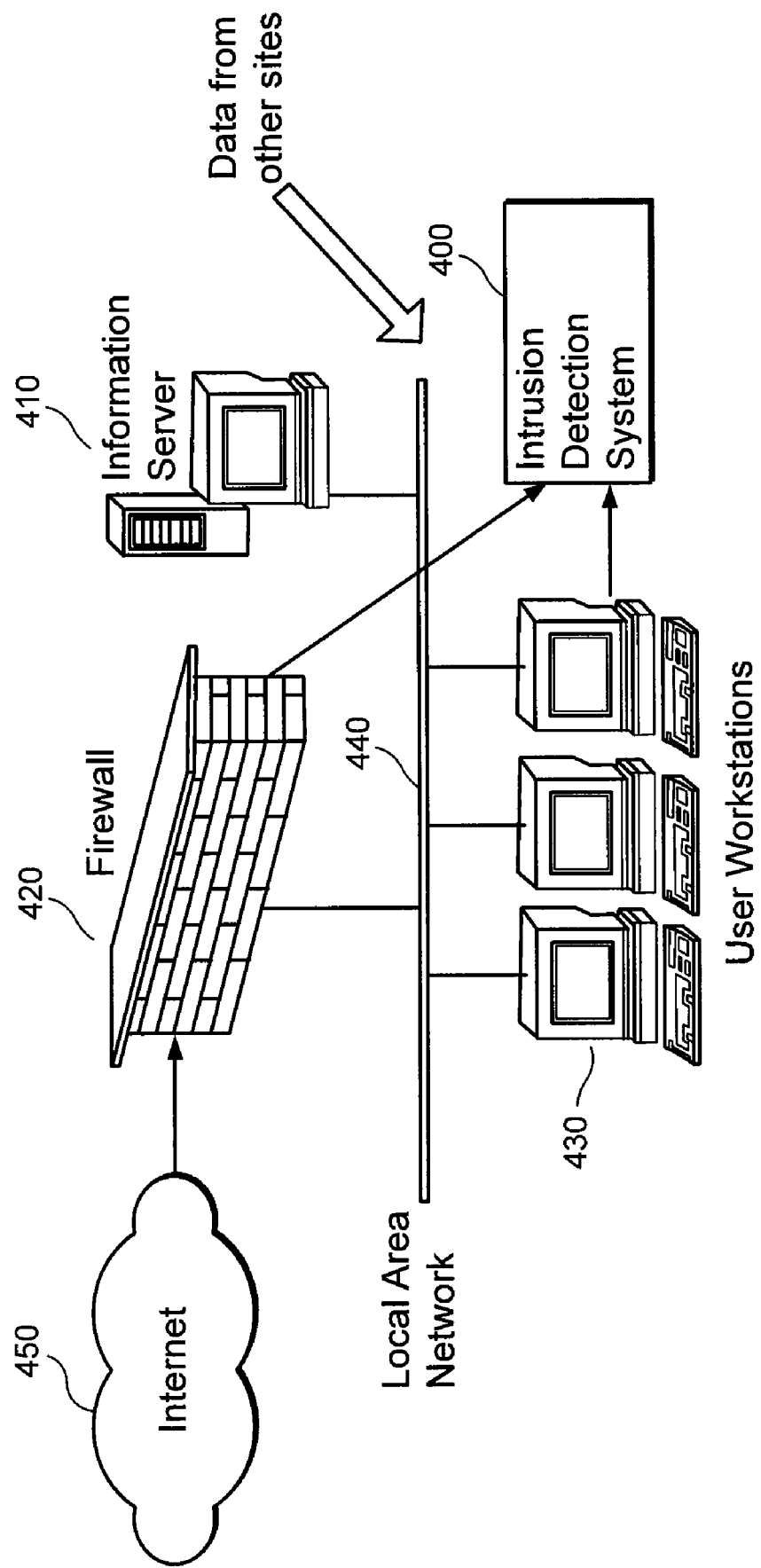
F I G. 5

METHOD AND SYSTEM FOR DATA CLASSIFICATION IN THE PRESENCE OF A TEMPORAL NON-STATIONARITY

CROSS REFERENCE TO RELATED APPLICATIONS

The present application is a continuation of U.S. patent application Ser. No. 10/276,429 filed Apr. 22, 2003 now U.S. Pat. No. 7,478,077 (the "'429 Application"), which is U.S. National Phase of International Application PCT/US01/15140 filed May 10, 2001 and published in English on Nov. 22, 2001 as International Publication No. WO 01/88834 (the "International Application"), the entire disclosures of which are incorporated herein by reference. The present application also claims priority from U.S. patent application Ser. No. 60/204,816 which was filed on May 17, 2000 (the "'816 Application"), the entire disclosure of which is incorporated herein by reference. This application claims priority from the '429 Application pursuant to 35 U.S.C. §120, from the International Application pursuant to 35 U.S.C. §365, and from the '816 Application pursuant to 35 U.S.C. §§119(e), 120 and 365.

FIELD OF THE INVENTION

The present invention relates to a method and system for classifying data, and more particularly to a data classification method and system in the presence of a temporal non-stationarity.

BACKGROUND INFORMATION

Approaches for predicting the value of a dependent response variable based the values of a set of independent predictor variables have been developed by practitioners in the art of the statistical analysis and data mining for a number of years. Also, a number of conventional approaches for modeling data have been developed. These known techniques require a set of restrictive assumptions about the data being modeled. These assumptions include, e.g., a lack of noise, statistical independence, time invariance, etc. Therefore, if the real data being modeled is dependant on certain factors which are contrary to the assumptions required for the accurate modeling by the conventional techniques, the results of the above-described conventional data modeling would not be accurate.

This is especially the case in the presence of temporal, non-stationary data. Indeed, no robust approach which considers such data has been widely used or accepted by those in the art of the statistical analysis. For a better understanding of the difficulties with the prior art approaches, temporal data and non-stationary data are described below.

Temporal data refers to data in which there exists a temporal relationship among data records which varies over time. This temporal relationship is relevant to the prediction of a dependent response variable. For example, the temporal data can be used to predict the future value of the equity prices, which would be based on the current and past values of a set of particular financial indicators. Indeed, if one believes in the importance of trends in the market, it is not enough to simply consider the current levels of these financial indicators, but also their relationships to the past levels.

In another example, the supermarket application may prefer to group certain items together based on the purchasers' buying patterns. In such scenarios, the temporal data currently used in such supermarket application is the data provided for each customer at the particular checkout, i.e., a single event. However, using the data at the checkout counter for a single customer does not take into consideration the past data for this customer (i.e., his or her previous purchases at the counter). In an example of an intrusion detection system, the use of the time-varying data is very important. For example, if a current login fails because the password was entered incorrectly, this system would not raise any flags to indicate that an unauthorized access into the system is being attempted. However, if the system continuously monitors the previous login attempts for each user, it can determine whether a predetermined number of failed logins occurred for the user, or if a particular is sequence of events occurred. This event may signify that an unauthorized access to the system is being attempted.

Non-stationary data refers to data in which the functional relationship between the predictor and response variables changes when moving from in-sample training data to out-of-sample test data either because of inherent changes in this relationship over time, or because of some external impact. For example, with a conventional network intrusion detection system, a predictive model of malicious network activity can be constructed based on, e.g., TCP/IP log files created on a particular network, such as the pattern formed from the previous intrusion attempts. However, intruders become more sophisticated in their attack scenarios, attack signatures will evolve. In addition, the conventional intrusion detection systems may not be usable for all conceivable current operating systems, much less for any future operating systems. An effective intrusion detection system must be able to take into consideration with these changes.

One of the main difficulties being faced by the conventional predicting engines is that the data is "multi-dimensional" which may lead to "over-fitting". While it is possible to train the prediction system to make the predictions based on the previous data, it would be difficult for this system to make a prediction based on both new data and the data which was previously utilized to train the system. The conventional systems utilize predictor values for each category of the data so as to train themselves as described above. For example, if the prediction system intends to predict the performance of certain baseball teams, it would not only use the batting average of each player of the respective team, but also other variables such as hitting powers of the respective players, statistics of the team while playing at home, statistics of the team when it is playing away from home, injury statistics, age of the players, etc. Each of these variables has a prediction variable associated therewith. Using these prediction variables, it may be possible to train the system to predict the performance of a given baseball team.

However, the conventional systems and methods described above are not flexible enough to perform its predictions based on a new variable (e.g., the number of player leaving the team) and a new corresponding prediction variable being utilized for the analysis. In addition, it is highly unlikely that the data values being utilized by the conventional systems and methods, i.e., after the system has already been trained, is the same as or similar to the data of the respective prediction variables that were already stored during the training of this system. The above-described example illustrates what is known to those having ordinary skill in the art as "over-fitting". As an example to illustrate this concept, the system may only be trained using training data (e.g., in-sample data) which can represent only 0.1% of the entire data that this system may be required to evaluate. Thereafter, the prediction model is built using this training data. However, when the system is subjected to the real or test data (e.g., out of sample data), there may be no correlation between the training data and the real or test data. This is because the system was only subjected to training using a small portion of the real/test data (e.g., 0.1%), and thus never seen most of the real or test data before.

There is a need to overcome the above-described deficiencies of the prior art systems, method and techniques. In particular, there is a need to provide a method and system for classifying data that is temporal and non-stationary.

SUMMARY OF THE INVENTION

A classification system and method according to the present invention offers an approach for a prediction in the presence of temporal, non-stationary data which is advantageous over the conventional systems and methods. The first exemplary step of the system and method uses temporal logic for discovering features provided in the data records. The next exemplary step is the classification of the data records using the selected features. Another exemplary step of the system and method of the present invention utilizes a "shrinkage technique" to reduce the undesirable effect of "over-fitting".

Accordingly, a method and system according to the present invention are provided for determining a feature of a particular pattern. Using these exemplary system and method, data records are received, and predetermined patterns that are associated with at least some of the data records are obtained. Using the system and method, particular information is extracted from at least a subset of the received data records, the particular information being indicative of the particular pattern for at least some of the data records. Then, it is determined whether the particular pattern is an unexpected pattern based on the obtained predetermined patterns. At least one record of the data records may include temporal data and/or non-stationary data.

In another embodiment of the present invention, the predetermined patterns are obtained by assigning a threshold, and correlating the data records into sets of patterns as a function of the threshold. Also, the determination of whether the particular pattern in an unexpected pattern include a determination if the particular pattern corresponds to at least one pattern of the sets of patterns. The positive determination regarding the unexpected pattern can be made if the particular pattern does not correspond to any pattern of the sets of patterns.

In yet another embodiment of the present invention, the unexpected pattern can be indicative of an interestingness measure in the predetermined pattern. In addition, the data records can include input sequences, and the input sequences can be scanned to determine an interestingness measure of at least one event in the input sequences. It is also possible to initialize a pattern list by inserting all events of the input sequences therein. Then, from all patterns in the pattern list, a first pattern which has a largest interestingness measure may be selected. The data records may include a maximum allowable length value. Thus, the first pattern can be expanded to be a second pattern. If a length of the second pattern is greater than the maximum allowable value, the second pattern can be added to the pattern list. Thereafter, if a length of the second pattern is less than or equal to the maximum allowable value, the first pattern can be subtracted from the pattern list. These steps can be repeated until the pattern list becomes empty. Finally the particular pattern which includes the interestingness measure can be output.

According to still another embodiment of the present invention, a pattern list may be initialized by inserting all events of the input sequences therein, and at least one suffix list can also be initialized. Locations of certain patterns of the input sequences can be calculated, and previously discovered may be updated patterns based on the calculated locations. The pattern list of the certain patterns can then be updated. The data records can include a maximum allowable length value.

In another embodiment of the present invention, further records are generated by modifying the data records to include additional features. Also, a functional model is generated using the further records. A plurality of sets of the further records are also generated, and the prediction model is generated for each set of the further records. Furthermore, a single model can be generated based on each functional model of the respective set of the further records.

According to yet another embodiment of the present invention, the data records which have the unexpected pattern can be classified. Thereafter, a prediction model is generated as a function of the classified data records. The classification of the data records can be performed using a Multivariate Adaptive Regression Splines technique. Then, data and/or parameters of at least one of the classified data records is shrunk so as to determine a mean of the data and/or the parameters. The shrinking technique can be a Stein's Estimator Rule technique.

BRIEF DESCRIPTION OF THE DRAWINGS

For a more complete understanding of the present invention and its advantages, reference is now made to the following description, taken in conjunction with the accompanying drawings, in which:

FIG. 1 is an exemplary embodiment of a classification system according the present invention;

FIG. 2 is a top level diagram of an exemplary embodiment of a method according to the present invention, which can be performed by the classification system of FIG. 1;

FIG. 3 is a flow diagram of a first exemplary feature selection technique of the method according to the present invention which performs the feature selection by utilizing a threshold to determine whether a particular pattern is an unexpected pattern;

FIG. 5 is an illustration of an exemplary implementation of the system and method of the present invention by an intrusion detection system;

DETAILED DESCRIPTION

Figure 4A:
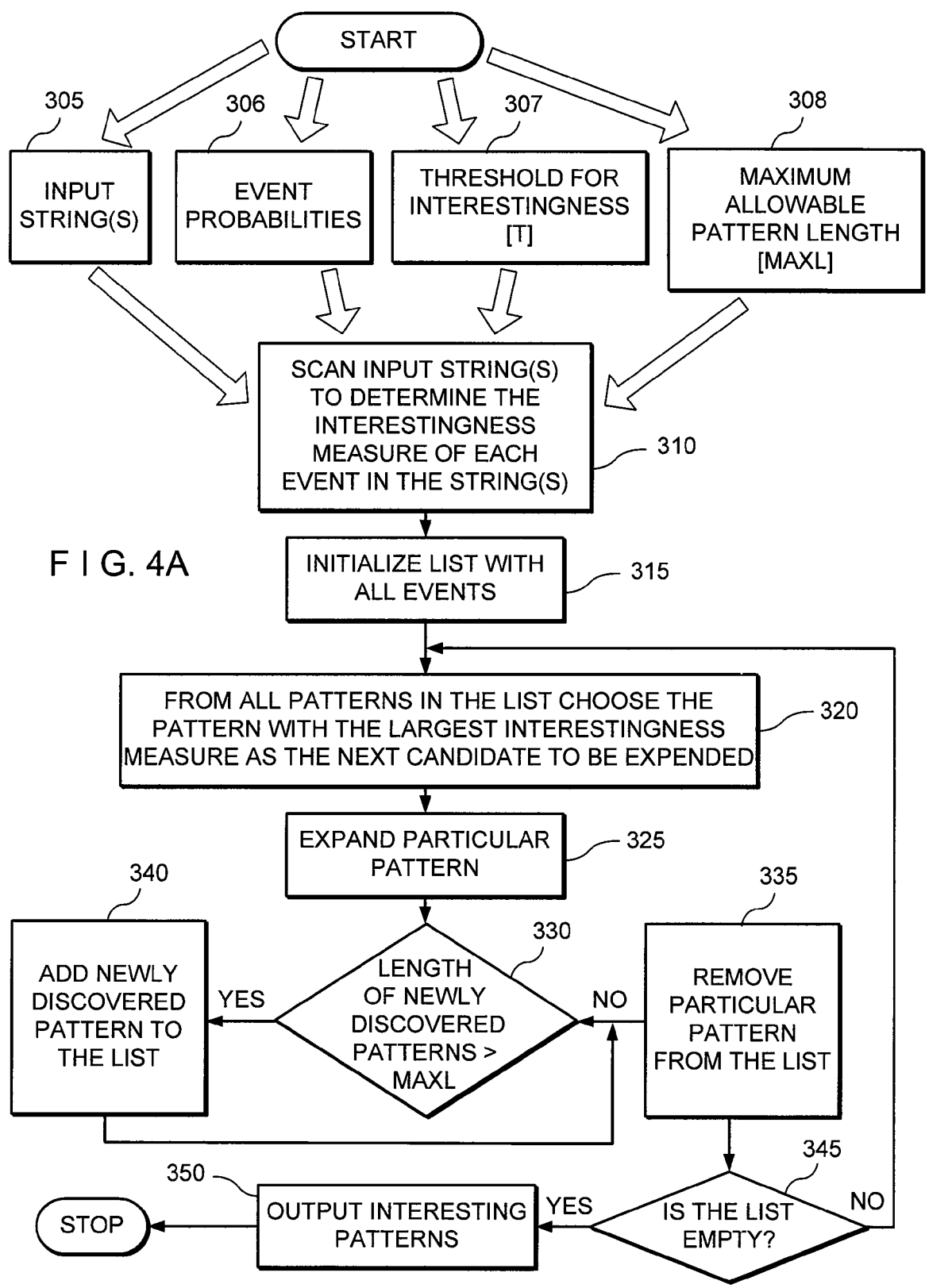
FIG. 4A is a flow diagram of a second exemplary feature selection technique of the method according to the present invention which performs the feature selection based on an interestingness measure.

FIG. 1 illustrates an exemplary embodiment of a classification system 10 according to the present invention. In this drawing, the system 10 is connected to one or more databases 20 for receiving an ordered set of data records. Each data record preferably includes a set of features that may be relevant (given particular domain knowledge) for predicting the value of a defined dependant variable. In addition, a particular data record may also include certain relationships between itself and other data records.

Upon the receipt of these data records, the system 10 according to the present invention selects and/or extract certain features from the data records, as shown in step 100 of FIG. 2, which illustrates an exemplary embodiment of the method according to the present invention. These features may be temporal features that are most relevant for predicting the value of the dependent variable. Then, in step 110, the system 10 uses the method of the present invention to classify and modify the data records received from the databases 20 based on the features that were extracted from the data records and the classification thereof. Since the classified data records being generated by step 110 are numerous, it is beneficial to shrink them. (step 120 of FIG. 2). Thereafter, the data records that were selected as including or being part of the particular patterns (when classified and shrunk) are used to generate a predictive model in step 130 of FIG. 2. Finally, the prediction model and/or the shrunk data records and patterns are output. For example, FIG. 1 illustrates that such output can be provided to a printer 30 for generating hard copies of the predicted model or shrunk data, forwarded to a display device 40, stored on a storage device 50, and/or transmitted via a communications network 60 to another device (not shown in FIG. 1).

According to one exemplary embodiment of the present invention, the system 10 can be a general purpose computer (e.g., Intel processor-based computer), a special purpose computer, a plurality of each and/or their combination. The storage device 50 can be one or more databases, one or more hard drives (e.g., stackable hard drives) internal RAM, etc. The communications network 60 can be the Internet, Intranet, extranet, or another internal or external network. It is also within the scope of the present invention to receive the data records from the databases 20 via a communications network, such as the Internet, Intranet, etc. The details of exemplary embodiments of the present invention are provided below.

I. FEATURE SELECTION

To accomplish the extraction/selection of the features from the data records, the classification system 10 searches and preferably selects certain patterns in the data records which can be defined as having an "interestingness measure". This particular interestingness measure used is preferably domain dependent, and in general, it is the measure of how much the occurrence of the pattern correlates with the occurrence of a single value of the predicted variable. The determination of the interestingness measure can be useful in a number of examples, such as, e.g., for a network intrusion detection. When searching for patterns that characterize malicious activity on the network, not only the patterns that occur frequently in the presence of an attack are monitored, but also the selection of those patterns which occur more frequently during an attack than during the normal network activity.

The above-described example defines at least one "interestingness feature" which can be used by the system and method of the present invention for monitoring the patterns of the data records having this measure, and selecting the corresponding patterns therefrom. For example, the interestingness measure for the network intrusion system may be a ratio of a number of occurrences of the particular pattern during the course of intrusion to the number of occurrences of this pattern during the course of normal network behavior. This interestingness measure, unlike the frequency, enables an identification of patterns that are non-frequent and yet highly correlated with intrusive behavior, and provides a way to ignore patterns which occur frequently during an intrusion, but occur just as frequently during normal behavior.

In another example of the network intrusion detection, the dependent variable that may be used for the interestingness feature can have a value between 0 and 1, which represents the probability that the associated data record that can be a part of the intrusion. In this exemplary case, the interestingness measure of a pattern P is denoted as:

$$I(P)=Pr(\text{Intrusion}|P).$$

The interestingness measure of the pattern P would, in this case, be the probability that the particular data record is part of the intrusion given that the pattern P occurred. Using a predefined interestingness threshold T, the following sets of patterns can be included in the data records as additional features:

$$S1=\{P|I(P)>T\}, S2=\{P|I(P)<1-T\}, S3=\{P|-P\in S2\}$$

For example, set S1 may represent the most interesting patterns. In the case of the intrusion detection, set S1 may be defined as a set of patterns that are most highly correlated with the intrusion based on the training of the prediction model using in-sample data. Set S2 may include the least interesting patterns, or in the exemplary intrusion detection, set S2 may represent the most highly correlated patterns with a normal behavior also based on the training of the prediction model using in-sample data. Set S3 may have the patterns whose negation is provided in set S2. The purpose of set S3 is to aid in the mitigation of the effects of non-stationarity.

For example, in the intrusion detection scenario, the system 10 and method according to the present invention take into consideration the situation in which the out-of-sample data set contains an intrusion that was not present in the in-sample data on which the model was based. Thus, as illustrated in FIG. 3, an exemplary embodiment of the present invention provides that the system 10 receives an ordered set of data records which includes the data records used for accessing the network (step 200), and assigns a predetermined interestingness threshold T to be applied to these data records (step 210). The data records are then correlated so that particular sets of patterns are associated therewith, based on the threshold T (step 220). In step 230, it is then determined whether the current pattern (e.g., a predetermined number of unsuccessful logins to the network) corresponds to the first type of an expected event that is provided in set S1. It would not be expected that the patterns that are part of this novel attack to be in set S1, since set S1 contains the patterns associated with only those attacks present in the training data (e.g., which used the in-sample data for generating the prediction model). If the current pattern corresponds to the patterns in set S1, then the pattern is assigned as being of the first type in step 240, i.e., definitely an intrusion attack on the network. Otherwise, it is determined (in step 250) whether the current pattern corresponds to the second type of an expected event that is provided in set S2.

If the current pattern corresponds to the patterns in set S2, then the pattern is assigned as being of the second type in step 260, i.e., definitely not an intrusion attack on the network. It would not be expected that the patterns that are part of this novel attack to be in set S2 because this set S2 contains the patterns that are associated with a normal behavior of the network (as trained by the in-sample data). However, if the current pattern does not correspond to set S1 or set S2, then there is a pattern that does riot neatly fit into any known set of patterns, i.e., thus being a novel attack. This pattern would not be considered as being a normal behavior on the network. According to this exemplary embodiment of the system and method according to the present invention, the pattern(s) present in the above described novel attack are considered as deviating from the patterns provided in set S2. Therefore, the current pattern has to be the third type of event i.e., an unexpected (or interesting) event, which should be part of the set S3 of patterns that were in neither set S1 nor in set S2. Thus, in step 270, the current pattern is set as including an interestingness feature so as to identify its behavior as deviating from what is considered as the normal behavior on the network, even if this deviant behavior is not part of any known attack. After the current pattern is set as described above with reference to steps 240, 260, 270, the determination regarding the type of the event (of the current pattern) is output in step 280.

Given that the data records are populated with both a set of basic features as well as the derived features, namely temporal patterns, a classifier based on this data can be generated.

From the above described exemplary method of the present invention, it should be understood that an interestingness measure for the patterns of the data records could be defined as marking such patterns "unexpected" patterns. To find unexpected patterns, it may be preferable to first define these patterns in terms of temporal logic expressions, in sequences of the data records. For example, it is possible to assume that each event in each data record in the sequence occurs with some probability, and that certain conditional distributions on the neighboring events are present. Based on such predicates, it is possible to compute an expected number of occurrences of a certain pattern in a sequence. If the actual number of the occurrences of a particular pattern significantly differs from the expected number of the occurrences, then this particular pattern would be considered "unexpected" and therefore interesting.

To determine the expected number of the occurrences of the particular pattern P, it may preferable to assign a probability distribution over the events according to one exemplary embodiment of the present invention. In general, certain problem domains may suggest a preferable technique to evaluate these expectations rather than by calculating them as a function of the frequencies of individual events. In the exemplary network intrusion detection setting, it is possible to calculate the expected number of the occurrences of the particular pattern P during the attack on the network based on the frequency of the particular pattern P during the normal activity on the network. In other settings, i.e., different than the network intrusion detection, other techniques for determining the expectations may be appropriate. The underlying issue solved by the system and method of the present invention is whether given any technique for computing the expectations for the particular pattern, it is possible to efficiently identify interesting or unexpected patterns using the retrieved data records.

In one exemplary technique of the method according to the present invention, all unexpected patterns can be found if, e.g., the ratio of the actual number of occurrences to the expected number of occurrences exceeds a certain threshold. This exemplary technique is illustrated in FIG. 4A. First, input string(s)/sequence(s) 305, event probabilities 306, a threshold T for the interestingness measure 307 and a number for a maximum allowable pattern length ("MAXL") 308 are provided to the system 10. The event probabilities 306 may be determined for each atomic event. The threshold T 307 may be a value that, if exceeded by the interestingness measure of a pattern, deems the pattern to be interesting. It is also possible to input a user-defined constant to the system 10 which determines the maximum number of events that a particular event or data record can precede another event or data record. Then, in step 310, the input string(s)/sequence(s) are scanned to determine the interestingness measure of each event therein. In step 315, a list L that includes all these events is initialized. From all patterns provided in the list L, a particular pattern C is selected which has the largest interestingness measure to be the next pattern for expansion (step 320).

Then, in step 325, this particular pattern C is indeed expanded by scanning the input string(s)/sequence(s) to detect the occurrences of the particular pattern C. When the occurrence of the pattern C is detected, the particular pattern C is expanded as a prefix and as a suffix, i.e., record all occurrences of: (C Op X) and (X Op C), where X is also a pattern, "Op" ranges over the temporal operators, and X ranges over all events. Thereafter, the interestingness or unexpected pattern(s) of all newly discovered patterns C' is determined, i.e., by the system 10 as described below.

In step 330, it is determined whether the length of the newly discovered patterns C' is smaller than the maximum allowable length (MAXL, and if so, the newly discovered patterns C' can be removed from the list L (step 340). Otherwise, the particular pattern C is removed from the list L in step 335. In step 345, it is determined whether the list L is empty. If not, the processing of this exemplary technique of the method according to the present invention is returned to step 320. Otherwise, in step 350, the interesting pattern(s) are output by the system 10, e.g., to the printer 30, the display device 40, the storage device 50 and/or the communications network 60.

In another exemplary embodiment of the present invention, it is possible to start with small patterns, and expand only those patterns that offer the potential of leading to the discovery interesting/unexpected, larger patterns. Using this exemplary technique, it is preferable to first find all patterns that occur relatively frequently, given a class of operators, an input sequence of events, and a frequency threshold. The exemplary technique for solving this problem has two alternating phases: building new candidate patterns, and counting the number of occurrences of these candidates.

The efficiency of this exemplary technique is based on two observations:

a. Where there are potentially a large number of patterns that have to be evaluated, the search space can be dramatically pruned by building large patterns from smaller ones in a prescribed way. For example if a pattern "αNβNγ" is frequent, then the patterns "αNβ" and "βNγ" must also be frequent. Thus, for a pattern P to be frequent, its sub-patterns should also be frequent. The exemplary technique for identifying frequent patterns can take advantage of this fact by considering the patterns of size n if its prefix and suffix of size n–1 are themselves frequent.

b. All complex patterns can be the result of recursively combining other smaller patterns. For example, in order to efficiently count the number of occurrences of the pattern "αNβ$B_\kappa$δ$B_\kappa$γ", it is preferable to identify the number of occurrences and location of the two patterns "αNβ" and "δ$B_k$γ", and to have an efficient way for combining the patterns via the $B_K$ operator. In general, since all of exemplary operators can be binary, when combining two patterns with operator Op to create a larger pattern and determine the number of occurrences of the resulting pattern, it is preferable to determine the number and locations of Op's two operands, and to provide an efficient way for locating patterns of the form A Op B.

The exemplary technique according to the present invention initially counts the number of occurrences of length 1 patterns (e.g., the length of the pattern is the number events that occur in it). Thereafter, a candidate set for the next iteration of discovery is computed by combining, in a pair-wise manner all frequent length-1 patterns via each operator. For example, in the nth iteration, the combination of the patterns of length n−1 and length 1 can be added to the candidate set provided that the length (n−1) prefix and suffix of the resulting length n pattern have already been deemed frequent in the previous iteration. Then, during the discovery phase, the number and location of the occurrences of the candidate length n patterns can be determined given the locations of their length n−1 prefixes and length 1 suffixes. This process continues until the candidate set (or list) becomes empty. The memory requirements of this exemplary technique are minimized because once a pattern is deemed as being infrequent, it can never result in being the sub-pattern of a larger frequent pattern, and can therefore be discarded. Such property may not hold in view of the definition of interestingness provided above, as shall be discussed in further detail below. In particular, a pattern can be unexpected while its component sub-patterns may be expected. This feature of the interestingness measure can be understood using the following example:

Let the set of events be E={A, B, C}. Assume that the probability of these events is Pr[A]=0.25; Pr[B]=0.25; and Pr[C]=0.50. Also assume that these events are independent. Let the interestingness threshold T=2, i.e., for a pattern to be interesting, the value of the actual number of occurrences of the pattern divided by the expected number of occurrences of the pattern should preferably exceed 2. For example, the following string of events can be input into the system 10:

ABABABABCCCCCCCCCCCC (the length of this string being N=20)

Given the above-mentioned probabilities, E[A]=5 and E[B]=5, and the expression for computing expectations for patterns of the form ANB.

$$E[ANB] = Pr[A]Pr[B](N-1)$$
$$= (0.25)(0.25)(19)$$
$$= 1.1875$$

Since A[A]=4 and A[B]=4, both of the events A and B are not interesting (in fact, the actual number occurrences of these events was less than what was expected), but the pattern ANB which occurred 4 times was interesting with $$IM(ANB) = \frac{4}{1.1875}$$
$$= 3.37$$

This lack of monotonicity in the interestingness measure can result in a significantly more. complex problem, specifically in terms of space complexity. In the exemplary technique for discovering frequent patterns, significant pruning of the search space may occur with each iteration. That is, when a newly discovered pattern is found to have occurred fewer times than the frequency threshold, it may be discarded as adding new events to it, and thus cannot result in a frequent pattern (which is not the case using the interestingness measure). The addition of an event to an uninteresting pattern can result in the discovery of an interesting pattern being created. This inability to prune the discovered patterns leads to a large increase in the amount of space required to find unexpected patterns.

Figure 4B:
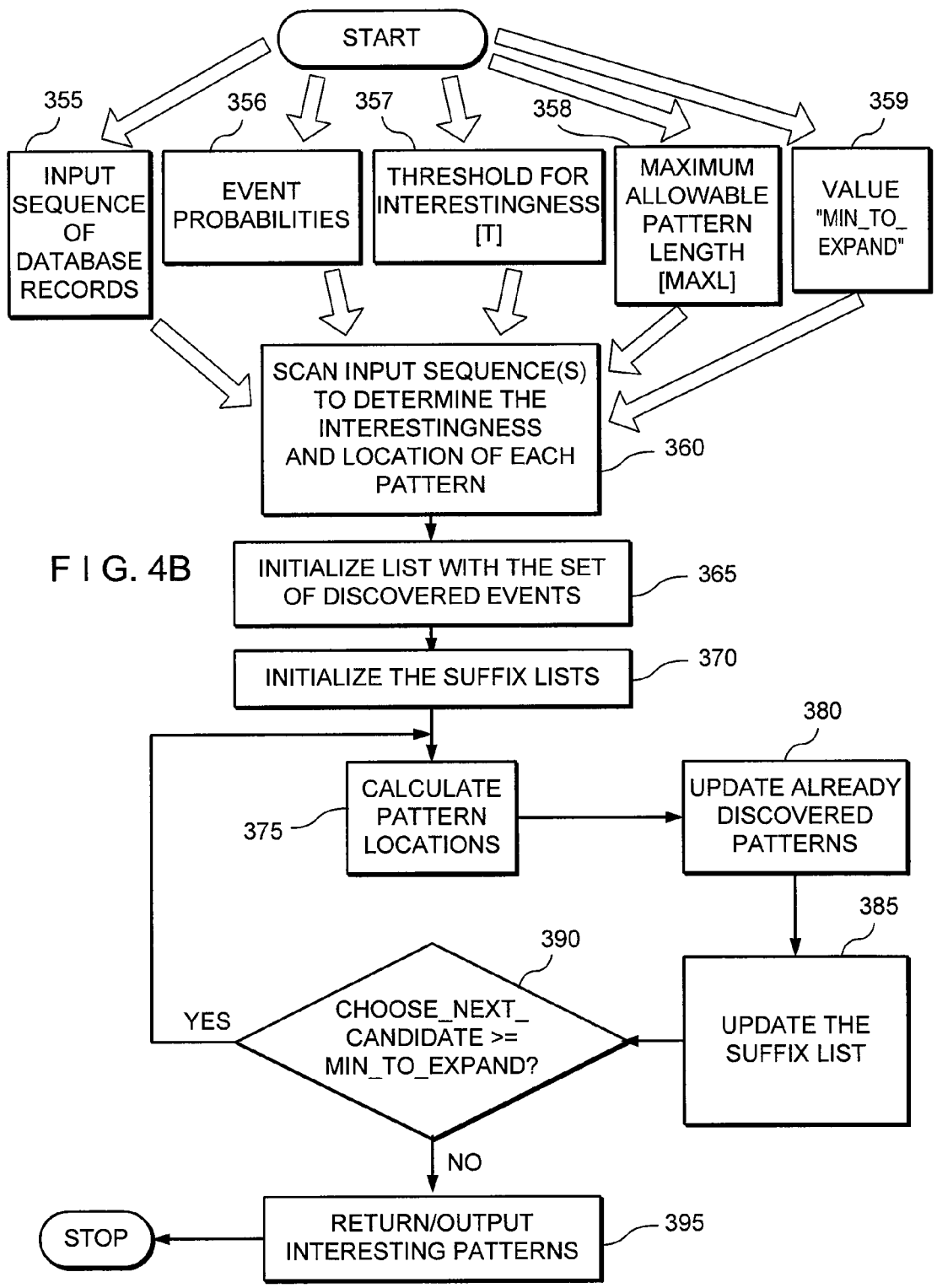
FIG. 4B is a flow diagram of a third exemplary feature selection technique of the method according to the present invention which performs the feature selection based on suffix lists.

Another exemplary technique of the method according to the present invention for finding unexpected patterns involves sequential scans over the string of events discovering new patterns with each scan is illustrated in FIG. 4B. To summarize this exemplary technique, a list is maintained of those patterns that were discovered previously, and on each subsequent iteration of this technique, the "best" pattern is selected from this list for expansion to be the seed for the next scan. Described below is an exemplary method to determine which pattern is the "best" pattern.

The "best" pattern can be defined as a pattern that is most likely to produce an interesting pattern during the expansion. By expanding the already interesting pattern, it is possible, and even likely, to discover additional interesting pattern(s). However, it should still be determined which is the best candidate for the expansion among interesting patterns already discovered. If no interesting patterns remain unexpanded, it is determined whether there any uninteresting patterns worth expanding.

According to this exemplary embodiment of the present invention, input string(s)/sequence(s) 355, event probabilities 356, a threshold T for the interestingness measure 357, a number for a maximum allowable pattern length ("MAXL") 358 and a value "MIN_TO_EXPAND" 359 are provided to the system 10. The MIN_TO_EXPAND value is preferably the minimum threshold of expected interestingness that the pattern should have in order to become the next pattern. Then, a scan of the input string(s)/sequence(s) takes place, in which the number of occurrences (and therefore, the frequencies) of individual events are counted to determine the interestingness and location of each event (step 360). This scan (e.g., a linear scan) is a scan of the "DL" events that occur in the record string(s)/sequence(s), where "D" is the number of data records and "L" is the number of fields in each data record.

In step 365, the list of patterns is initialized with the set of discovered patterns. For example, certain R lists should be initialized at this stage, where R is the number of temporal operators that are used. Each list may represent the pattern form X, where X is an arbitrary literal. One sorted list can be stored for each temporal operator. The processing time and capacity preferable for this initialization corresponds to the processing time and capacity of sorting these lists. Initially, all lists can be sorted in an identical order. Therefore, the total processing time and capacity of this initialization may be defined by O (N log N), where N is the number of distinct events in the database. Each literal α, in each list, has an initial candidacy value of:

$$\frac{A[\alpha]}{P[\alpha]}$$

where A[α] is the number of occurrences of a which can be determined in the initial scan.

Then, in step 370, the suffix lists are initialized. For example, the "R" lists are preferably initialized at this stage, where R is the number of temporal operators that can be predefined or defined by a user. Each such list contains the potential suffixes for all length 2patterns. Each of these lists would again be sorted based on their candidacy values. Initially, these candidacy values are the same as those for the set of discovered patterns (described above for step 465), and therefore no additional sorting is necessary. The total processing time and capacity of this initialization can be defined as O(N).

In step 375, the pattern locations are calculated. As described above, it its possible to compute the locations of the pattern resulting from combining the pattern P with a literal α via the operator "Op" via the linear scan of the location lists for the pattern P and the literal α. The total number of operations that should be performed for this computation is proportional to the longer of these two location lists. This has an expected value of:

$$\frac{DR}{N},$$

where D is the number of data records, R is the number of temporal operators, and N is the number of distinct events in the database.

Then, the already discovered patterns are updated in step 380. Given that the locations of the candidate P Op α have been previously computed, this step entails two substeps. In the first substep, the newly discovered patterns are inserted into the appropriate R lists. Since it is preferable to maintain the sorted order of these lists, each such insertion uses the formula O(log(L)), where L is the length of the list into which the pattern P is being inserted. The second substep is to update the list that P was chosen from. The number of occurrences of the pattern P yet to be expanded via the operator op has been previously decreased by the number of occurrences of the pattern P Op the literal α. This will reduce its candidacy value and the pattern P. Therefore, the pattern P should be restored to its appropriate sorted position. This operation utilizes O(L) operations where L is the length of the list from which the pattern P was selected.

In step 385, the suffix list is updated. In particular, the list corresponding to the form of the pattern P Op the literal α should be updated. The total number of patterns of this form already discovered should be increased by the number of occurrences J of the pattern P op the literal α. Additionally, the number of the literal α's yet to be used as a suffix for a pattern of this form should be decreased by the same value J. Further, since the candidacy value of the literal α is being decreased, the candidacy value should be put in its appropriate sorted order. This will require O(N log N), where N is the number of distinct events in the database.

Thereafter, in step 390, it is determined whether the output from the function "CHOOSE_NEXT CANDIDATE" is greater than or equal to the value of MIN_TO EXPAND. The function CHOOSE_NEXT CANDIDATE determines M values that result from multiplying the candidacy value for each of the patterns $P_i$ (which are provided at the beginning of the discovered pattern lists times) by the first value in the suffix matrix for the pattern form. For example, the result is obtained for a combination of the pattern $P_i$ from the set of discovered patterns with the literal α via the operator Op corresponding to the operator for the list from which the pattern P was taken. The pattern $P_i$, the literal $α_j$ and the operator Op are chosen whose combination results in the largest amongst these M values. The time and capacity of this operation can be expressed as O(M). If the result obtained from the function CHOOSE_NEXT CANDIDATE is greater than or equal to the MIN_TO_EXPAND value, then the processing of the method according to the present invention returns to step 375. Otherwise, the interesting and/or unexpected patterns are returned/output to the printer 30, the display device 40, the storage device 50 and/or the communications network 60, and the processing of this exemplary method is completed.

For example, the exemplary technique described above with reference to FIG. 4B continues to expand best candidates of the unexpected patterns until there are no more candidates that are worthy of expansion. To further explain this concept, the following definitions can be utilized:

Definition I: The FORM(P) of the pattern P is a logical expression with all ground terms in the pattern P replaced by variables. For example, if $P=αNβB_Kγ B_Kδ$, then FORM $(P)=WNXB_KYB_KZ$.

Given the length of the input string(s)/sequence(s), it is possible to determine the number of patterns of each form in the input string/sequence. For example, given a string of length M, the number of patterns of form XNY is M−1. The number of patterns $XB_KY$ is (M−K)K+((K)(K−1)/(2)).

Definition II: Given the pattern P and an operator Op, Actual Remaining (P Op X) is the number of patterns of the form P Op X that have yet to be expanded. This value is maintained for each operator Op and the pattern P. That is, a value for PNX; PBKX; XBKP, etc. is maintained. X ranges over all events. For example, if there are 20 occurrences of $P=αB_Kβ$ in the input string and 5 patterns of the form $αB_KβNX$ have been discovered so far, then Actual Remaining Next $αB_KβNX$=15.

The following heuristic can be used to determine which discovered pattern is the best pattern to use for the expansion. Given an. arbitrary literal D, the best pattern P for the expansion is preferably the pattern for which the value of E[[A[P Op δ]/E[P Op δ]] is the maximum for some δ.

This heuristic can be a probabilistic statement that the pattern P (which is most likely to result in the discovery of an interesting pattern) is the pattern for which there exists a literal δ. In particular, the expected value of the interestingness measure of the pattern generated when the literal δ is added to the pattern P via one of the temporal operators Op is the highest over all discovered patterns P, literals δ and operators Op. It is preferable to use the expected value of the interestingness measure because, although the actual number of occurrences of both the pattern P and the literals δ is known, the number of occurrences of P Op δ is not known. This expectation is computed preferably directly from the previously-described derivations of expectations, and can be described using the following example:

If P=αNβ, and Op is "next",
   then E[A[PNδ]/E[PNδ]]
      = (#$P_N$)(FR(δ))=Pr[α]Pr[β]Pr[δ](K−2)
   where, K = length of input string,
      FR(δ) = frequency of the literals' δ that could complete the pattern __N_NX, and
      #P N = number of occurrences of the pattern P yet to be expanded via the operator N.
If Op is "before", then
   E[A[$PB_K$δ]=E[$PB_K$δ]]
      = ((#P)(FR(δ))("BEFOREK"))/
      Pr[α]Pr[β]Pr[δ](K−2)("BEFOREK")

-continued

= ((#P)(FR(δ)))/Pr[α]Pr[β]Pr[δ](K−2)
where BEFOREK is a user defined variable that is equal to the maximum distance between two events X and Y for $XB_KY$ to hold.

Similar arguments can be used for any combination of the operators Op of "before", "next", and "until". In general, the candidate pattern P, the suffix, the literal δ and the operator Op are chosen whose combinations are most likely to result in the discovery of the interesting pattern.

Throughout the above-described technique and with reference to FIG. 4B, two data structures should be used to efficiently compute best candidates on each subsequent iteration.

a. An ((N+1)×M) matrix where N is the number of distinct events, and M is the number of different pattern forms that are intended to be discovered. For example, M can be very large. However, it is preferable to limit the length of the patterns to approximately 5 (depending on the application), taking into consideration that the infrequency of much larger patterns typically makes them statistically insignificant. With the maximum pattern length set to 5 and using four temporal operators N, Bk, U, and ^, the value of $$m = \sum_{i=1}^{5} 4^i = 4\frac{(4^5 - 1)}{(4-1)} = 1364,$$

which is a manageable number.

The structure of this matrix can be follows: each entry [i, j] i ∈ 1 ... N, j ∈ 1 ... M represents the remaining number of yet-to-be-discovered patterns having the form j whose final event is i. This number can be easily maintained because it is the total number of occurrences of the event i minus the number of already discovered patterns of the form j whose final event is i. The additional (N+1) row contains the total number of already discovered patterns (i.e., the sum of the values in the columns) of the form j. Each column of this array can be sorted such that literal α precedes β in the column j if the number of the literals α remaining to be added as suffixes to create patterns of the form j divided by Pr[α], exceeds that value for the literal α. This value can be called the "candidacy value" of the corresponding literal for the corresponding pattern form. The matrix can be called the "suffix matrix".

b. The second data structure is an array of M×R lists where M is again number of different pattern forms that should be discovered and R is the number of temporal operators being used. In list $j_{op}$, all patterns of the form j that have already been discovered are maintained in a sorted order by the number of the occurrences of each pattern yet to be expanded through the use of the operator Op divided by E[P]. This value can be called the corresponding pattern's "candidacy value" for the corresponding operator. Such value is simple to calculate since the total number of patterns that have the form P Op X is known. Along with each pattern, it is possible to maintain the number of occurrences of the given pattern P, and the locations of the pattern P. This array can be termed the "set of discovered patterns."

The best combination of an element from each of these two data structures. may be the candidate for the next discovery iteration. For example, at each iteration, it is possible to assume that the first value in each list in the set of discovered patterns of whose length is less than the maximum allowed pattern length corresponds to the patterns $P_1, P_2, \ldots, P_M$. Additionally, it is possible to assume that the first value in each column in the suffix matrix may correspond to the literals $\alpha_1, \alpha_2, \ldots, \alpha_M$. The M values that result from multiplying the candidacy value are computed for each of these patterns $P_i$ times the first value in the suffix matrix for the pattern form that is the result of combining the pattern $P_i$ from the set of discovered patterns with the literal α via the operator Op corresponding to the operator for the list from which the pattern P was taken. The pattern $P_i$, literal $\alpha_j$ and operator Op can be selected whose combination results in the largest value among these M values. In doing so, the goal of selecting the candidate pattern, literal, and operator whose combination is most likely to result in the discovery of an interesting pattern can be accomplished. Once these candidates have been selected, the determination of the number of occurrences of the pattern $P_i$ Op $\alpha_j$ can be computed via linear scans of the location lists for the pattern $P_i$ and the literal $\alpha_j$. For example, if Op=N, then it is possible to look for locations 1 such that $P_i$ occurs at the location 1 and $\alpha_j$ occurs at location 1+1. If Op=^, it is possible to look for the locations where both $P_i$ and $\alpha_j$ occur. One of the ways to initiate the above-described procedure is by choosing the variable triple (i.e., pattern, literal, operator) whose combination would most likely result in the discovery of an interesting pattern. As the procedure progresses, if the given pattern P has not generated many newly discovered patterns as a candidate for the expansion, the pattern will preferably percolate toward the top of its associated sorted list. Likewise, if a literal α has not been used as the suffix of many discovered patterns, the literal will percolate to the top of its suffix list. In this way, as patterns and literals become more likely to generate an interesting pattern, via the combination, and they will become more likely to be chosen as candidates for the next iteration.

II. CLASSIFICATION OF DATA

Turning back to the method of the present invention illustrated in FIG. 2, the data obtained in the feature selection step is classified (step 110). The classification of data has been problematic to those having ordinary skill in the art of data mining. The most widely utilized classification technique entails the use of decision trees. There are more powerful classification techniques (in the sense that the decision trees are able to represent a more robust class of functions) such as neural networks. However, those having ordinary skill in the art often do not use the neural networks for classifying data because the neural networks are computationally complex, and lack transparency. One of the important features of a classifier is that the resulting function should ultimately be understandable. It is preferable to understand why a prediction made by the classifier was made to better understand relationships that exist in current problem domain. The neural networks are a black box, and while their predictions may be accurate, they lead to little insight about the problem at hand.

The present invention uses an alternative technique known as "MARS" (Multivariate Adaptive Regression Splines). The detailed description of MARS is described in, e.g., in J. Friedman, "Multivariate Adaptive Regression Splines", The Annals of Statistics, Vol. 19, No. 1, 1991 pp. 1-141. MARS is a nonlinear technique that overcomes many of the shortcomings of standard decision trees while being computationally tractable and ultimately interpretable.

Although the recursive partitioning may be the most adaptive of the methods for multivariate function approximation, it suffers from some significant restrictions that limit its effectiveness. One of the most significant of these restrictions is that the approximating function is discontinuous at the sub-region boundaries (as defined by splits in the nodes). It severely limits the accuracy of the approximation, especially when the true underlying function is continuous. Small perturbations in the predictor variables can potentially result in widely varying predictions. Additionally, decision trees are poor at approximating several simple classes of functions such as linear and additive functions. The records obtained from the feature selection are augmented by a set of temporal features. For example, from the data records having 9 features to the data having 200 features (i.e., a high dimensional data).

Since all classification techniques generate models based on in sample data that are designed to perform well on out of sample data and because of the resultant high-dimensionality, the issue of over-fitting may occur as described below.

III. BIAS INCREASE VIA SHRINKAGE

In all classification techniques, the introduction of additional degrees of freedom reduces the in sample error (bias) of the model while increasing the model variance. This frequently results in poor approximations of out of sample data. To address this problem, some classification methods include a technique for reducing the model bias, typically via a reduction in the classification model's degrees of freedom. This reduction in degrees of freedom increases bias in the classification model, while reducing its variance and out-of-sample error.

The combination of the forecasts can be done by averaging resulting in a maximum likelihood estimator ("MLE"). To evaluate the applicability and usefulness of this approach, it is possible to consider the more general situation of trying to estimate a parameter $\Theta$ by $t(x)$. For example, if $E[t(x)]=\Theta$, then $t(x)$ can be an unbiased estimator of $\Theta$ and a measure of the precision of this estimator may be $E[t(x)-\Theta]^2$, i.e., its variance. Instead, if $E[t(x)]\neq\Theta$, then $t(x)$ is a biased estimator of $\Theta$. A measure of its precision is still $E[t(x)-\Theta]^2$, but because $E[t(x)]\neq\Theta$, this quantity is not the variance, and known as the mean squared error. Thus, $$E([t(x)-\Theta]^2) = E([t(x)-E[t(x)]+E[t(x)]-\Theta]^2)$$
$$= E([t(x)-E[t(x)]]^2) + (E[t(x)]-\Theta)^2 + 2(E[t(x)]-\Theta)$$
$$E[t(x)-[t(x)]]$$
$$= E([t(x)-E[t(x)]]^2) + (E[t(x)]-\Theta)^2$$
$$= \text{var}[t(x)] + (E[t(x)]-\Theta)^2$$
$$= \text{var}[t(x)] + [\text{Bias}(t)]^2$$

By sacrificing an increased bias for a decreased variance, it is possible to achieve a uniformly-smaller MLE. Stein's estimator, now known as Stein shrinkage, described in B. Efron et al., "Stein's Estimation Rule and its Competitors—An Empirical Bayes Approach", Journal of the American Statistical Assoc., Vol. 68, March 1973, pp. 117-130, was originally developed for the case of reducing bias in linear functions. The results of the Stein's estimator can be extended for the nonlinear case. For example, by "shrinking" the estimated parameters towards the sample mean, this approach mitigates the effects of non-stationarity by reducing the impact of deviations in the distributions of the estimator variables between in-sample and out-of-sample data.

Thereafter, in step 130 of FIG. 2, the prediction model is generated from the data records on which feature section was performed, and/or which were classified and then shrunk. Finally, in step 140, such prediction model and/or the classified and reduced data are output to the printer 30, display device 40, storage device 50 and/or communications network 60.

IV. EXEMPLARY APPLICABILITY OF THE PRESENT INVENTION

The system and method according to the present invention can be used in two exemplary settings, e.g., a network intrusion detection and a disease classification. Embodiments of the present invention for each of these exemplary settings are discussed below.

A. Network intrusion detection addresses the problem of detecting intrusions on a computer network. In summary, the training data may consists of a set of TCP/IP records that have been scored 0/1 depending on whether that connection was part of an attack as well as with the specific attack type. The intrusion detection system then learns features that distinguish normal from malicious network activity. These features then become the input to a classifier which when run on out-of-sample data scores each record based on the likelihood that it is part of an attack. Finally, the third stage is to combine the classifiers that result from training on many in sample training sets as well as to mitigate the problems of over-fitting and non-stationarity.

FIG. 5 shows one such exemplary intrusion detection system ("IDS") 400 according to the present invention. First, data is collected in the form of log-files that consist of a sequence of records about activity on the network. The log files can be collected via a local area network 440 from an information server 410, an attached firewall 420, user workstations 430 and/or other sites. One record can be created for each connection that occurs. The information in each record may include time and date of the connection, the type of service provided, the source and destination ports, the source and destination IP addresses, the duration of the connection, and other data.

Figure 6:
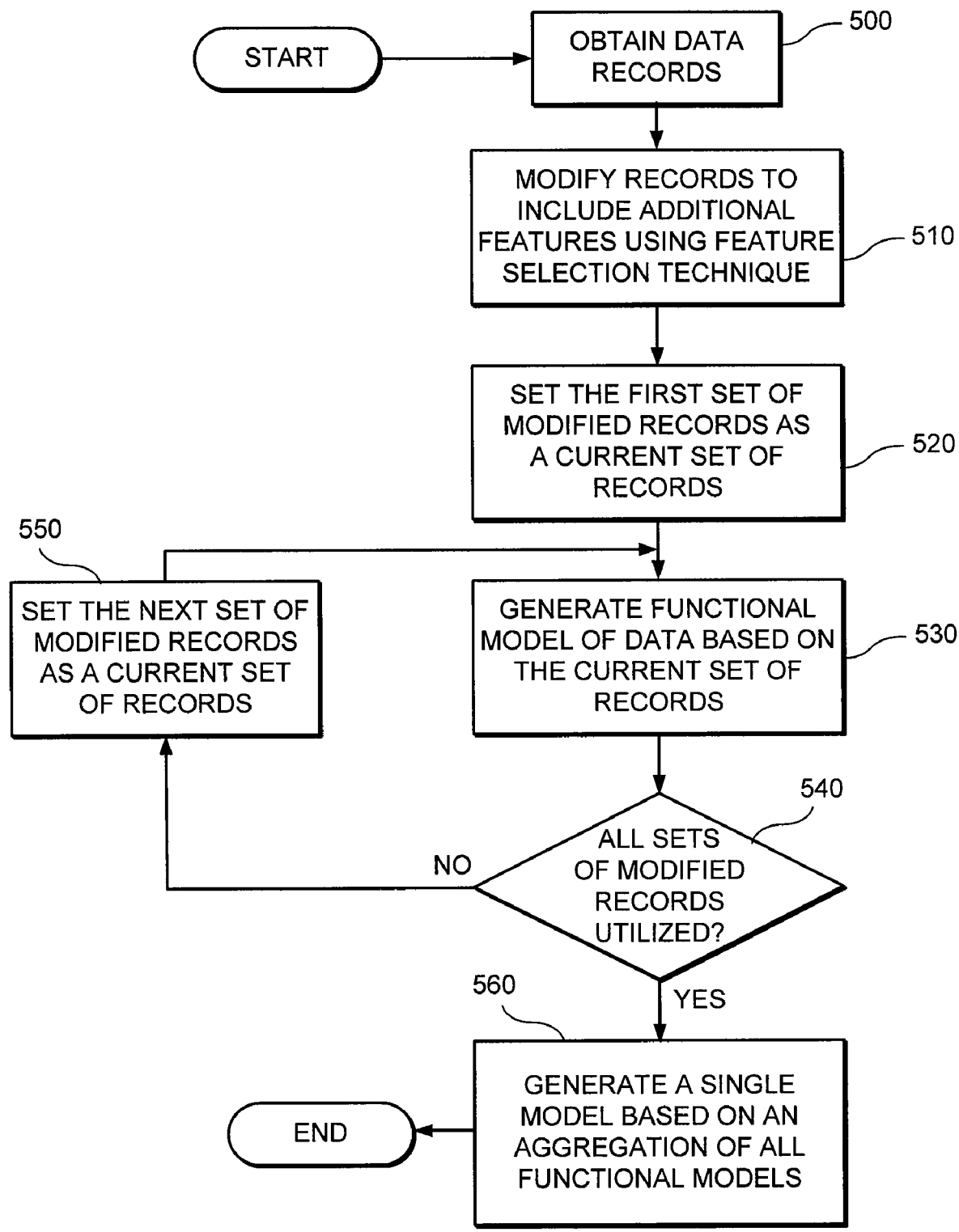
FIG. 6 is a flow diagram of the exemplary embodiment of the method of the present invention utilized by the intrusion detection system of FIG. 5, in which a prediction model is generated.
Figure 7:
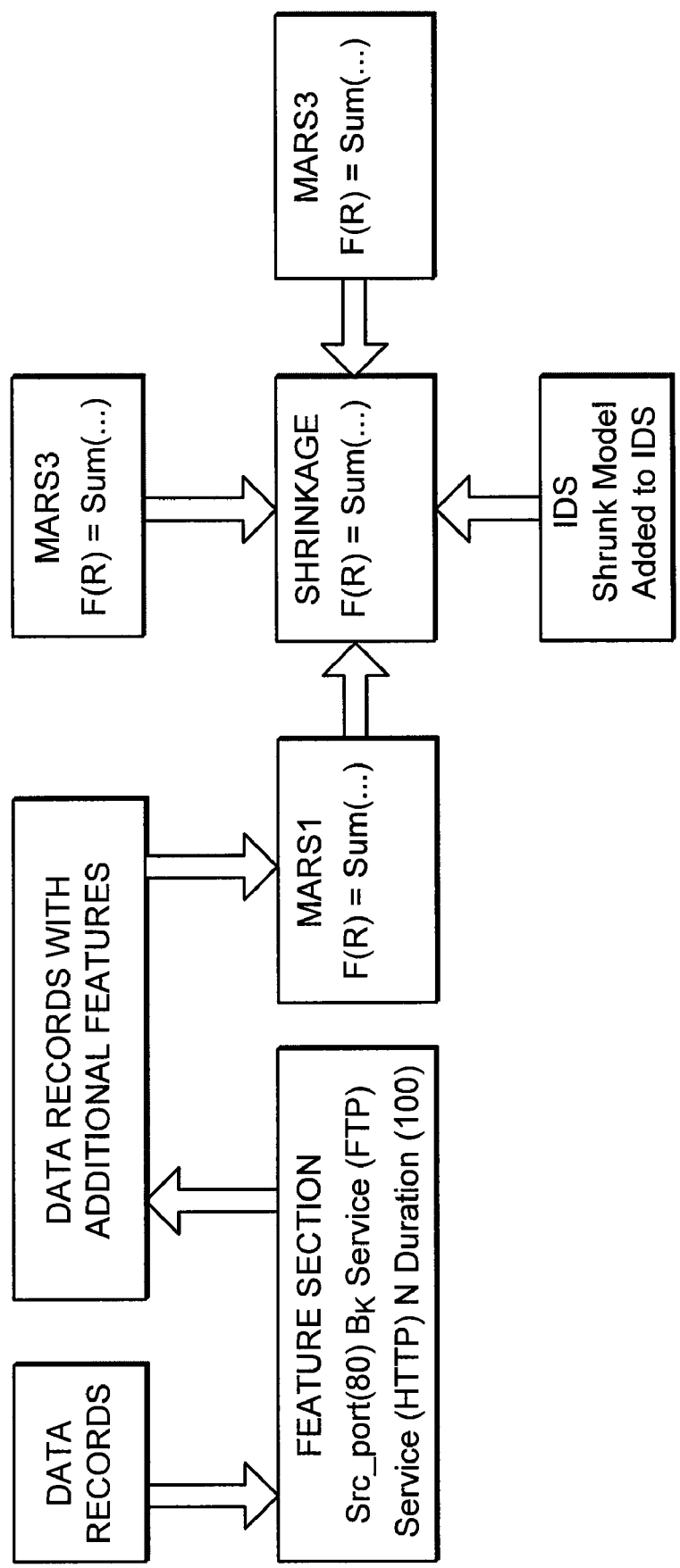
FIG. 7 is another flow diagram of the exemplary implementation of the method of the present invention by the intrusion detection system of FIG. 5.

The IDS 400 described above serves two purposes, e.g., data collection and network activity monitoring, and intrusion identification. In serving these roles, the IDS 400 may include or be connected to a large database (e.g., the storage device 50) for data storage, and a computational engine for scoring individual network activity records based on their likelihood of being part of an intrusion. In the training phase and as illustrated in FIG. 6, the IDS accumulates the data generated at the various monitoring points on the network (step 500). The aggregated data records are then scored manually, e.g., with a score of 1 indicating that the given record was part of a network attack and a score of 0 indicating that the record was part of normal activity. This exemplary embodiment of the present invention may use, e.g., scored data generated by the Defense Department's Advance Research Project Agency (DARPA). Once collected, this data becomes the input to the IDS 400, as shown in further detail in FIG. 7. The initial set of data records represents the input to the first stage of the technique, i.e., feature selection. In this stage a set of additional features (typically several hundred) are generated and added to each data record (step 510). The first set of data records are set as the current data records in step 520, and the current data records are input to the second stage of the technique—classification, i.e., MARS. MARS generates a functional model of the data capable of predicting intrusions on out-of-sample data based on the current data records (step 530). Then, in step 540, it is determined whether all sets of the modified data records were utilized. If not, in step 550, the next set of the modified data records is set as the current set of records, and the process returns to step 530 so that a number of functional models are generated. This set of models is then input into the final stage of the technique, i.e., shrinkage. Shrinkage results in the generation of a single model based on the aggregation of all of the predictor models generated (step 560). This is done in a way to mitigate the effects of non-stationarity in the data. This final model is then incorporated into the IDS 400. In the IDS 400, the model monitors network activity, identifying activity that is part of an (attempted) intrusion on the network. Concurrently, the IDS 400 may accumulate data records generated by the network monitors for use as future training data to the model. This allows the system and method of the present invention to continuously update itself based on changes in the types of activity occurring on the network.

B. In the disease classification, the main focus can be on cancer. Given that cancer results from changes in the DNA of healthy cells, the present invention provides an approach to cancer classification based on the gene expression. Both the cancer classification problem as well the class discovery problem are addressed by identifying discrepancies in gene expression between healthy and cancerous cells. It is then possible to evaluate the quality of the approach of the system and method according to the present invention to cancer classification by considering RNA samples from both healthy individuals as well as samples from patients from multiple known cancer classes as identified by their histopathological appearance for accurately and consistently validating the diagnosis made by hematopathologists on the genetic grounds. This is achieved by training the system (as described below) on RNA samples that are properly labeled by their cancer class (or labeled as being healthy). By discovering the genetic differences among cancer classes, a predictive model of theses classes is generated which can then be tested via cross validation and through testing on out of sample data, and a class discovery can be performed. For example, the system is trained on the same RNA samples. This time, however, these samples are unlabeled. The classes associated with each sample are discovered lo without a prior knowledge of this information. Additionally, novel classes within these samples are discovered.

Figure 8:
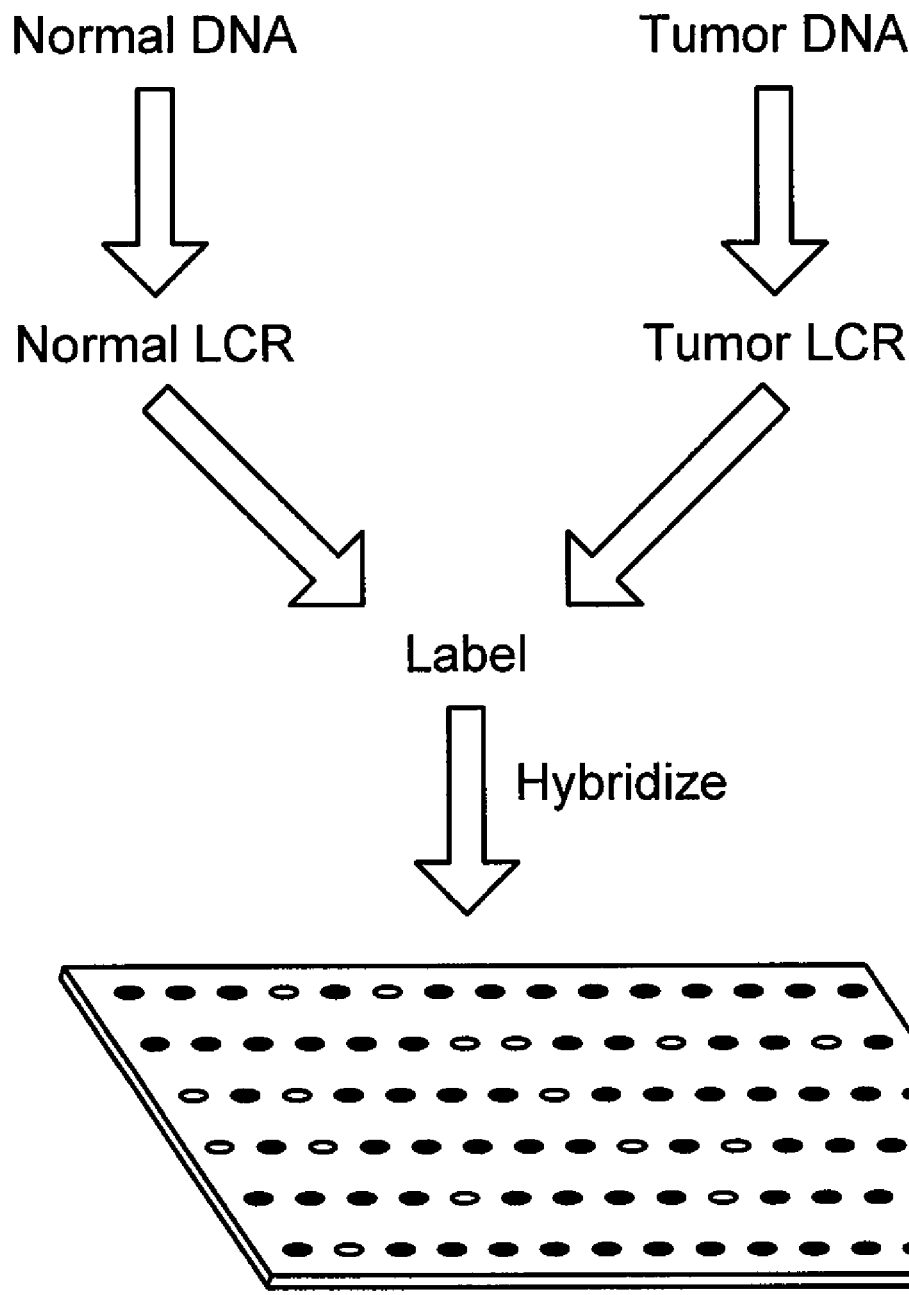
FIG. 8 an illustration of an exemplary implementation of the system and method of the present invention by a disease classification system.

As shown in FIG. 8, healthy DNA and cancerous DNA can each be dyed different colors and hybridized on a micro-array containing thousands of genes expected to be relevant to cell growth and regulation. Through this process, the expression levels of these targeted genes can be compared between the healthy and cancerous cells. The cancer classifier then constructs a model capable of classifying future DNA samples as either healthy or cancerous. Additionally, DNA samples from two different cancer types can be hybridized and a model constructed that identifies the cancer type of an out-of-sample, cancerous DNA strand. Through this process, the system is first capable of determining whether or not a DNA sample is cancerous, and if it is then identifying the associated cancer type. These results improve the targeting of treatment to specific cancer types. Described below is a description of how to distinguish between healthy and cancerous DNA, although the process may not be identical for identifying specific cancer types.

Figure 9:
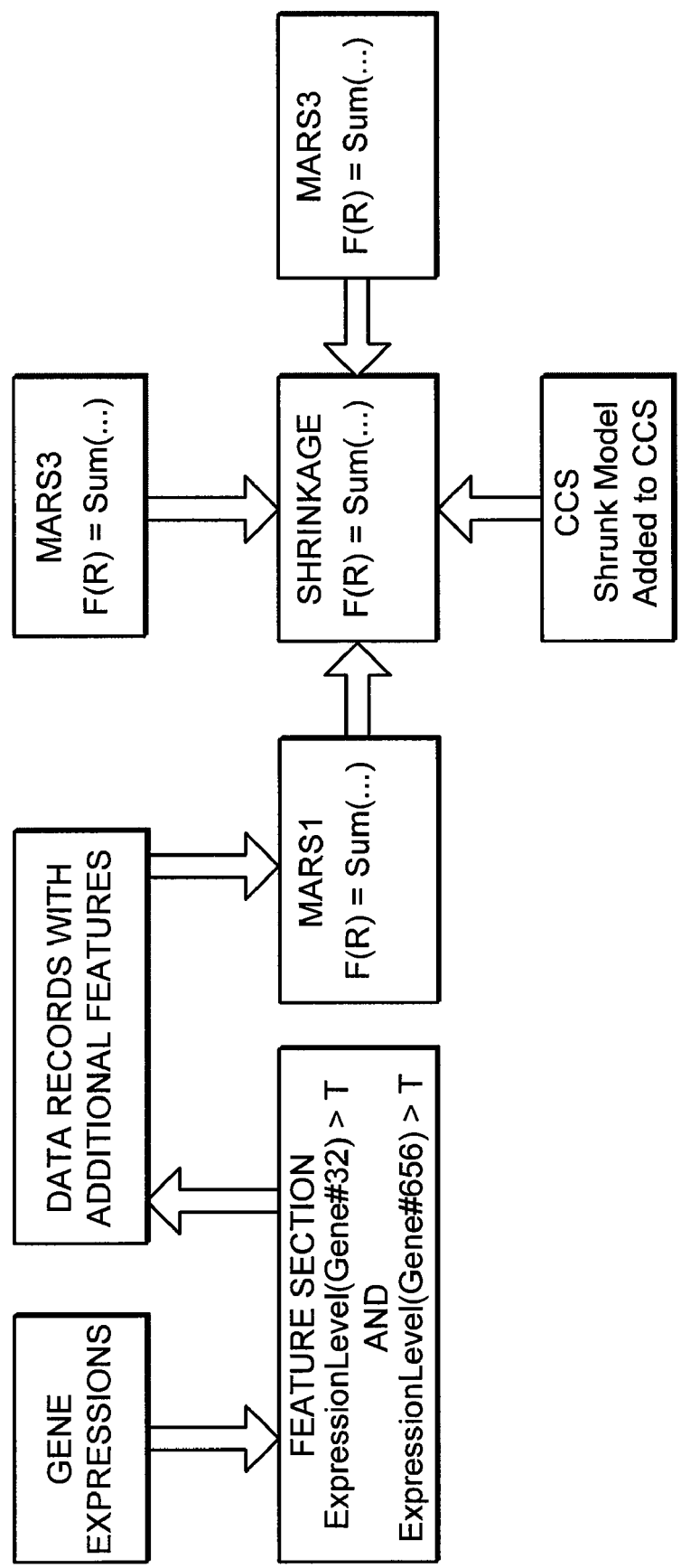
FIG. 9 is a flow diagram of the exemplary implementation of the method of the present invention by the disease classification system of FIG. 8.

The data collected from the micro-array is a set of gene expression. levels for both normal and cancerous DNA in thousands of different genes. Once collected, this data becomes the input to the cancer classification system (CCS) (see diagram below). As shown in FIG. 9, the set of expression levels represents the input to the. first stage of the method and system according to the present invention, i.e., feature selection. In this stage a set of features (typically several hundred) are generated. These features represent relevant relationships between the expression levels of different genes in terms of their ability to distinguish healthy from cancerous DNA. An example of a potential feature is, e.g., ExpressionLevel (Gene#32)>T AND ExpressionLevel(Gene#656)>T. This feature provides that both the expression levels of gene number 32 and number 656 exceed some threshold, and may be included if it represented a situation that is either highly correlated with healthy or highly correlated with cancerous DNA. Thus, such features are input to the second stage of the technique, i.e., MARS. MARS generates a functional model of the data capable of distinguishing between healthy and cancerous DNA on out-of-sample data. This process is typically executed several times on different training data sets, thus generating several models. This set of models is then input into the final stage of the technique, i.e., shrinkage. Shrinkage results in the generation of a single model based on the aggregation of all of the predictor models generated. The combination of models is particularly relevant to cancer classification when attempting to build a model that differentiates between several cancer types. Models are initially constructed to distinguish between pairs of cancer classes. Shrinkage then combines these models to create a single monolithic classifier capable of distinguishing between many different cancer classes.

One having ordinary skill in the art would clearly recognize that many other domains and applicable example in which data is temporal and/or non-stationary in nature can benefit using this system and method for classification according to the present invention. Indeed, the present invention is in no way limited to the exemplary applications and embodiments thereof described above.

The invention claimed is:

1. Computer-accessible medium which includes a set of software instructions for determining a feature of a particular pattern, wherein, when the software instructions are executed by a processing arrangement, the processing arrangement is configured to execute procedures comprising:

a) receiving data records, wherein at least one record of the data records includes non-stationary data;

b) obtaining particular patterns that are associated with at least some of the data records; and c) determining whether the particular pattern is an unexpected pattern based on the obtained particular patterns, wherein the processing arrangement is configured to at least one of display at least one result of the determination or record the at least one result, wherein the data records include input sequences, wherein, and in step (c), the processing arrangement is programmed:

i. scan the input sequences to determine an interestingness measure of at least one event in the input sequences, and ii. select a particular pattern derived from the particular patterns which has a largest interestingness measure;

wherein at least one portion of at least one of the particular patterns is expressed using at least one temporal logic expression.

2. Computer-accessible medium according to claim 1, wherein, when the processing arrangement executes the software instructions, the processing arrangement is further configured to extract particular information from at least a subset of the data records, the particular information being indicative of the particular patterns for at least some of the data records.

3. Computer-accessible medium which includes a set of software instructions for determining a feature of at least one of particular patterns, wherein, when the software instructions are executed by a processing arrangement, the processing arrangement is configured to execute procedures comprising:
   a) receiving at least one data records;
   b) obtaining the particular patterns that are associated with at least some of the at least one data record, wherein the obtaining the particular patterns includes correlating the data records into sets of patterns as a function of a threshold; and
   c) determining whether the at least one of the particular patterns is an unexpected pattern based on the obtained particular patterns,
   wherein the processing arrangement is configured to at least one of display at least one result of the determination or record the at least one result, and
   wherein at least one portion of the particular patterns is expressed using at least one temporal logic expression.

4. Computer-accessible medium according to claim 3, wherein, when the processing arrangement executes the software instructions, the processing arrangement is further configured to extract particular information from at least a subset of the at least one data records, the particular information being indicative of the particular patterns for at least some of the at least one data records.

5. The computer-accessible medium according to claim 3, wherein, when the processing arrangement executes the software instructions, the processing arrangement is further configured to execute procedures comprising:
   (d) obtaining a first set of patterns comprising at least one pattern based on the at least one data record; and
   (e) using at least one temporal operator, combining one or more patterns from the first set of patterns to generate a second set of patterns, wherein the one or more patterns selected from the first set of patterns meets a predetermined interestingness measure.

6. The computer-accessible medium according to claim 5, wherein the predetermined interestingness measure is the largest interestingness measure of a plurality of interestingness measures which exceeds a predetermined threshold.

7. The computer-accessible medium according to claim 5, wherein the combining procedure is performed in n number of stages on successively longer patterns.

8. The computer-accessible medium according to claim 7, wherein, in the $n^{th}$ stage of the combining procedure, patterns having a length of n−1 and patterns having a length of 1 are combined with one another.

9. The computer-accessible medium according to claim 8, wherein the patterns having a length of n−1 and patterns having a length of 1 are combined as a prefix and a suffix of an expression comprising the at least one temporal operator.

10. The computer-accessible medium according to claim 5, wherein, when the processing arrangement executes the software instructions, the processing arrangement is further configured to execute a procedure of determining a subset of patterns from the second set of patterns based on the predetermined interestingness measure.

11. The computer-accessible medium according to claim 5, wherein, when the processing arrangement executes the software instructions, the processing arrangement is further configured to execute a procedure of identifying an unexpected subset of patterns from at least one of the first set of patterns or the second set of patterns.

12. The computer-accessible medium according to claim 11, wherein a pattern is considered to be unexpected if a ratio of an actual number of occurrences of the pattern to an expected number of occurrences of the pattern is above a predetermined threshold.

13. The computer-accessible medium according to claim 12, wherein the expected number of occurrences of a pattern is based on a probability distribution, and the probability distribution is based on the at least one data record.

* * * * *